(12) United States Patent
Jia et al.

(10) Patent No.: US 6,326,209 B1
(45) Date of Patent: Dec. 4, 2001

(54) MEASUREMENT AND QUANTIFICATION OF 17 KETOSTEROID-SULFATES AS A BIOMARKER OF BIOLOGICAL AGE

(75) Inventors: Qi Jia, Arvada; Mei-Feng Hong, Northglenn; Stephen Cherniske, Boulder, all of CO (US)

(73) Assignee: Univera Pharmaceuticals, Inc., Broomfield, CO (US)

( * ) Notice: Subject to any disclaimer, the term of this patent is extended or adjusted under 35 U.S.C. 154(b) by 0 days.

(21) Appl. No.: 09/479,619

(22) Filed: Jan. 7, 2000

(51) Int. Cl.$^7$ ................................... G01N 33/00
(52) U.S. Cl. .................. 436/98; 436/817; 548/321.5
(58) Field of Search ................... 436/817, 98; 548/321.5

(56) References Cited

PUBLICATIONS

Adlercreutz et al. (1986 Supplement) Int. J. Sports Med. 7:27.
Clemmons and Van Wyk (1984) J. Clinics in Endocrinol. and Metabol. 13:113.
Dehennin et al. (1998) Steroids 63:80.
Field et al. (1994) J. Clinics in Endocrinol. and Metabol. 79:1310.
Furuya et al. (1998) Jpn. J. Clin Pathol 46:529.
Gelato and Frost (1997) Endocrine 7:81–85.
Kroboth et al. (1999) J. Clin Pharmacol 39:327.
Lobo et al. (1981) Obstet Gynecol 57:69–73.
Nishikaze and Furuya (1998) J. UOEH 20:273.
Obminski and Stupnicki (1997) J. Sports Med. Phys. Fitness 37:50.
Setchell et al. (1976) J. Steroid Biochemistry 7:615.
Shackleton et al. (1990) Steroids 55:472.
Tegelman et al. (1992) Int. J. Sports Med. 13:424.
Van Wyk (1984) in *Hormonal Proteins and Peptides,* vol. XII, (Li, C.H. ed.) Academic Press, NY, pp 82–125.
Vervoorn et al. (1992) Eur. J. Apppl. Physiol. 64:14.
Zhang and Henion (1999) Anal. Chem. 71:3955.

Primary Examiner—Jill Warden
Assistant Examiner—Monique T. Cole
(74) Attorney, Agent, or Firm—Swanson & Bratschun, L.L.C.

(57) ABSTRACT

The present invention provides an improved method for using the measurement of total urinary 17 KS-S, referred to herein as the urinary Anabolic/Catabolic Index (ACI), as part of a biomarker for biological age.

4 Claims, 8 Drawing Sheets

I   R = H
II   R = SO$_3$Na
III   R = C$_6$H$_9$O$_7$

IV   R = SO$_3$Na
V   R = C$_6$H$_9$O$_7$

VI   R = SO$_3$Na
VII   R = C$_6$H$_9$O$_7$

VIII   R = SO$_3$Na
IX   R = C$_6$H$_9$O$_7$

X   R = SO$_3^-$ Pyridine$^+$

I  R = H
II  R = SO$_3$Na
III  R = C$_6$H$_9$O$_7$

IV  R = SO$_3$Na
V  R = C$_6$H$_9$O$_7$

VI  R = SO$_3$Na
VII  R = C$_6$H$_9$O$_7$

VIII  R = SO$_3$Na
IX  R = C$_6$H$_9$O$_7$

X  R = SO$_3^-$ Pyridine$^+$

MEASUREMENT AND QUANTIFICATION OF 17 KETOSTEROID-SULFATES AS A BIOMARKER OF BIOLOGICAL AGE

FIELD OF INVENTION

The present invention relates generally to the use of the urinary Anabolic/Catabolic Index (ACI), that includes a measurement of total urinary 17 ketosteroid sulfates (17 KS-S), as part of a biomarker for biological age. Included in the present invention is an improved method for the measurement of total urinary 17 ketosteroid sulfates (17 KS-S).

BACKGROUND OF THE INVENTION

More than three decades ago, Hans Selye developed the stress-response model of aging. He described a progressive degeneration in which the organism ultimately fails to recover from the physical, mental and emotional effects of stress. To this day, Selye's model is accepted as one of the lynch pins of aging research. Brain degeneration, once thought to be an "inevitable" consequence of aging appears to be directly related to stress hormone levels. Dr. Robert Sapolsky, a MacArthur Fellow and Stanford biologist, found strong evidence that chronic emotional and oxidative stress, and not aging per se, causes brain degeneration. Current research indicates stress-related factors in Alzheimer's disease and other disorders.

Stress, whether physical, emotional or biochemical, produces alterations in hormone levels. Specifically, stress causes an increase in blood levels of corticosteroids, such as cortisol and a decrease in androgenic steroids, such as testosterone. Elevated levels of stress hormones have been determined to exert powerfully negative effects on the immune system, and may account significantly for age-related increases in auto-immune disorders such as lupus, multiple sclerosis, rheumatoid arthritis, fibromyalgia and chronic fatigue syndrome.

The terms anabolic and catabolic are commonly used in physiology to denote the build-up and break-down functions of both cells and tissues or entire systems. The Anabolic/Catabolic Index (ACI) test measures and reports the ratio of anabolic and catabolic activity in humans. It is a global/snapshot view of repair and rebuild (anabolic) activity versus waste activity (catabolic). It is important not to confuse this analysis with cellular catabolism, which refers to the biochemical reduction of compounds to create energy. For example, the breakdown of complex carbohydrates to yield glucose is a catabolic process. The ACI test, on the other hand, assesses the building up or tearing down of structural tissues, such as, muscle and other connective tissue.

Stress produces alterations in the anabolic/catabolic index, and may be influenced by factors favoring anabolic (recovery) activity. Simply measuring blood levels of cortisol (17-OHCS), also referred to as hydrocortisone, has been considered as a biomarker for catabolic activity. However, this measurement does not provide sufficient information to be relied on for this purpose. Cortisol, is the major corticosteroids hormone secreted by the adrenal cortex. The clinical usefulness of cortisol measurement is limited by the fact that stress induces a biphasic response in the secretion of cortisol. At some point of adrenal exhaustion, cortisol levels decrease even though the individual continues to deteriorate.

Various researchers have used the ratio of serum testosterone and cortisol as an anabolic/catabolic index (Adlercreutz et al. (1986) lnt. J. Sports Med. 7:27–28; Obminski and Stupnicki (1997) J. Sports Med. Phys. Fitness 37:50–55), while others use the ratio of non-SHBG-bound testosterone (NST) to cortisol (Tegclman et al. (1992) Int. J. Sports Med. 13:424–430) to measure the ACI. Recent research, however, suggests that neither testosterone nor NST is an ideal biomarker for catabolic activity. The measurement of testosterone produces inconsistent results in females (Vervoom et al. (1992) Eur. J. Appl. Physiol. 64:14–21), and is not reflective of alterations in IGF and IGFBP which contribute to the catabolic state. (Gelato and Frost (1997) Endocrine 7:81–85). IGF-I has also been used as an anabolic biomarker (Van Wyk (1984) in Hlormonal Proteins and Peptides, vol. XII, (Li, C. H. ed.) Academic Press, N.Y., pp 82–125), but turned out to be unreliable due to its hypersensitivity to shout-term changes in caloric intake, sleep and exercise. (Clemmons and Van Wyk (1984) J. Clin. Endocrinol. Metab. 13:113–143).

Urinary 17 ketosteroids (17-KS) consist primarily of 17 KS sulfate conjugates (17 KS-S) and 17 KS glucuronides (17 KS-G), the latter derived from cortisol, DHEA (dehydroepiandrosterone) and testosterone. (See FIG. 1). The measurement of steroids in human serum and urine specimens has been utilized as a clinical indicator of adrenal function (Lobo et al. (1981) Obstet Gynecol, 57:69–73), androgen abuse (Dehennin et al. (1998) Steroids 63:80) and as a indicator of general health (Field et al. (1994) J. Clin. Endocrinol. Metab. 79:1310). Researchers at Hokkaido University in Japan have recently proposed that a more comprehensive biomarker for anabolic activity is the measurement of total urinary 17 ketosteroid sulfate conjugates (17 KS-S). (Nishikaze and Furuya (1998) J. UOEH 20:273). This biomarker, which is comprised of four different hormone metabolites (DHEA-S, androsterone, etiocholanolone and epiandrosterone, see FIG. 1) reflects the full range of anabolic repair/rebuild activity in muscles, organs, connective tissue, immune and nervous systems. The amount of 17-KS-S from 24-hour secretion corrected with creatinine has been found to parallel the recovery from infection, illness, injury and psychosocial stress. (Van Wyk (1984) in Hormonal Proteins and Peptides, vol. XII, (Li, C. H. ed.) Academic Press, N.Y., pp 82–125; Furuya et al. (1998) Jpn. J. Clin. Pathol 46:529–537).

Dehydroepiandrosterone (DllEA), also referred to as, dehydio-3-isoandrosterone or 3-β-hydroxyandrost-5-ene-7-one, is a weakly androgenic steroid secreted primarily by the adrenal gland. It is one of the principal components of urinary 17-ketosteroids. DHEA(S) hydrosteroid sulfatases convert DHEA to DHEA-S. DHEA and DHEA-S levels correlate to stress, central nervous system function, immunological function, cardiovascular disorders and insulin sensitivity. (Kroboth et al. (1999) J. Clin. Pharmacol. 39:327).

The results of steroid profiling confirm that the measurement of total ketosteroids in the urinary steroid sulfate fraction represent only metabolites of anabolic activity. Therefore, factoring out the glucuronides gives a more precise indication of pure anabolic activity, which provides a sensitive and accurate picture of repair and rebuild activity in both women and men.

One method used to measure 17-KS-S levels involves a calorimetric assay (Zimmerman chromogen reaction). Although this method is widely used, it does not differentiate between ketosteroids nor between free and sulfate or glucuronide fractions. Additionally, the Zimmerman reaction also measures a significant amount of the degradation and conversion products resulting from peripheral glucocorticoid and testosterone metabolism; that is compounds having a $C(O)CH_2$ group not only at C17, but also at C3, C6 and C20. To obtain a true anabolic biomarker, glucocorticoid and other metabolites must be removed.

A second method currently used to measure 17-KS-S levels involves chromatographic separation followed by colorimetric reaction, which is outlined below and described in Example 1. (Setchell et at. (1976) J. Steroid Biochemistry 7:615–629).

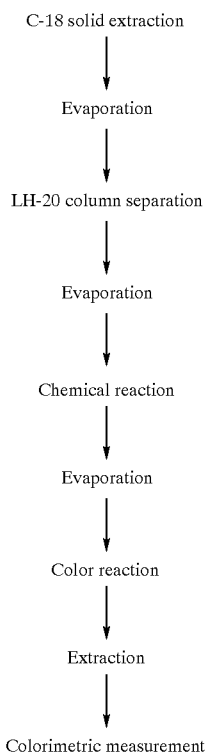

Although this method is specific for 17 KS-S, it is a time consuming process (involving two chromatographic separations) and it is expensive. This has been used as a research rather than a diagnostic method. More recently, mass spectroscopic detection conjugated with gas chromatography (GC) or high pressure liquid chromatography (HPLC) has been reported for quantification of 17-detosteroid conjugates (Shackleton et al. (1990) Steroids 55:472) and estrogen sulfates (Zhang and lienion (1999) Anal. Chem. 71:3955).

Urinary 17 KS-S levels are high in young, healthy individuals, decrease with aging and failing health, clearly decline with advancing disease and reach very low levels in severe disease and old age. This biomarker, therefore, provides a snapshot view of the body's regenerative capacity and "biological age." Although there is no established definition of "biological age," this term is frequently used to described the functional status of the human body as opposed to its chronological age. Current methods used to determine biological age include, measurement of skin thickness, strength, stamina, body composition, reaction time, vision, hearing, blood and neurological tests. All of these tests have one common feature, in that they measure aspects of anabolic and catabolic activity not as an active kinetic process, but rather as a clinical endpoint. To date, there has been no quantified correlation between 17 KS-S levels and biological age.

SUMMARY OF THE INVENTION

The present invention includes a method for using the measurement of total urinary 17 KS-S as a biomarker for biological age, in the index referred to herein as the urinary anabolic/catabolic index (ACI).

The method of this invention correlates 17 KS-S levels to biological age. Normal ranges of 17-KS-S/ACI, referred to herein as the "clinically derived standard range of 17-KS-S/ACI" have been established for different age groups, expanding the application of the ACI to reflect biological age. Comparison of the ACI of a person of a particular age group, to the clinically derived standard range of 17-KS-S/ACI, for that particular age group provides an indication of the biological age of that subject. Additionally, as the data base increases, it is anticipated that important associations may be revealed between ACI levels and specific disease states.

The ACI is also useful for a benchmark evaluation of healthy individuals. A variety of diet, lifestyle and nutritional supplement interventions can produce changes in hormones such as 17 KS-S, cortisol, catecholamines and insulin. Without having to conduct an entire battery of tests, the ACI can be used to reflect both positive and negative influences on this critical hormone balance.

The present invention includes an improved method for the measurement of total urinary 17-KS-S levels. Such method comprises: elution of a sample containing 17-KS-S through a C18 cartridge; filtration of the material eluted from the C18 cartridge; separation of the filtered material by HPLC or GC and analysis by mass spectrometry. The advantages of this method over the current methods are that it is specific for 17 ketosteroid-sulfates and it is a short process, involving only one extraction. This method can be used for both research and diagnostic purposes.

It is to be understood that both the foregoing general description and the following detailed description are exemplary and explanatory only and are not restrictive of the invention as claimed.

DETAILED DESCRIPTION OF THE INVENTION

The present invention includes a method for the using the measurement of total urinary 17 ketosteroid sulfate (17 KS-S) levels as part of a biomarker for biological age, referred to herein as the urinary anabolic/catabolic index (ACI).

The present invention includes a new system for measuring the biological age of an individual. The system of this invention is based on the determination of a person's Anabolic/Catabolic Index or ACI. The ACI of the present invention is a measurement of the concentration in the individual's urine of 17-ketosteroid sulfates over the concentration of creatinine. The present inventors have found that the ACI can be quantified in such a manner that the measurement of an individual's ACI can be used as a reliable indicator of the individual's biological age.

Although others have recognized that levels of 17-KS-S vary depending on a person's age—levels decreasing as an individual ages, it was not recognized that 17-KS-S levels could be incorporated into a Anabolic/Catabolic Index and employed as a highly useful biomarker of biological age.

According to the present invention, the ACI of a large number of individuals constituting a range of ages was determined. From this data, a range of ACI values was determined associated with certain age ranges of individuals. Based on this quantification of data, it is possible for an individual's biological age to be evaluated based on the ranges of ACI values that their ACI fits. For example, a 50 year old individual may find that their ACI value falls within the range of values that have been predetermined to be associated with individuals having a much older chronological age.

The present ACI information is useful. therefore, as a static measure of an individual's biological age. The longitudinal evaluation of an individual's ACI, in conjunction with treatments aimed at decreasing the biological age of an individual, provides an excellent method for monitoring the success or failure of given treatment regimes. For example, an individual or group of individuals will have their ACI measured prior to initiating a new diet, vitamin program or exercise protocol. As the treatment regime is instituted, the effects of the treatment on the individual's biological age can be easily monitored. This type of instantaneous monitoring can inform the decision-making) process as to whether a given treatment is effective or ineffective, and also can help provide feedback with respect to dosing and duration of treatment.

Certain terms used to describe the invention herein are defined as follows:

As used herein "biological age" refers to the functional status of the human body as opposed to its chronological age. Specifically, as used herein "biological age" refers to one's metabolic status as it relates to the ratio of anabolic and catabolic activity.

Figure 1:
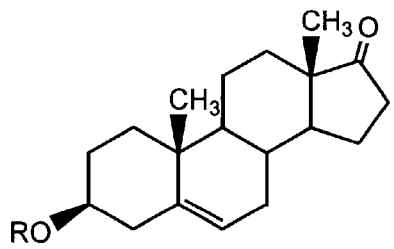
FIG. 1 depicts the structures of 17 ketosteroids present in urine. (I) dehydroepiandrosterone (DHEA), (II) dehydroepiandrosterone-3-β-sulfate (DHEA-S), (III) dehydrocpiandrosterone-3-β-glucuronide (DHEA-(G), (IV) epiandrosterone-3-β-sulfate, (V) epiandrosterone-3-β-glucuronide, (VI) androsterone-3-β-sulfate, (VII) androsterone-3-β-glucuronide, (VIII) etiocholanol-17-one-3-β-sulfate, (IX) etiocholanol-17-one-3-β-glucuronide and (X) 7-keto-dehydro-epiandrosterone-3-β-sulfate pyridine salt.
Figure 1:
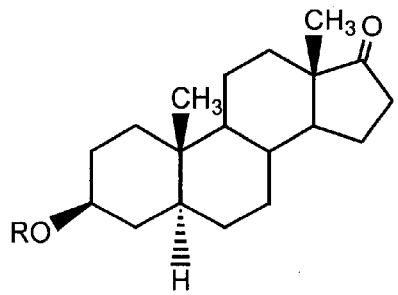
Figure 1:
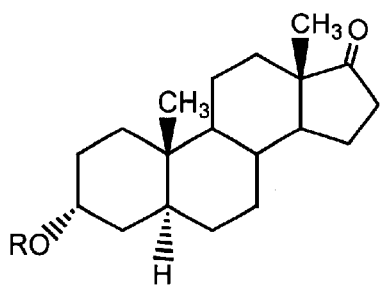
Figure 1:
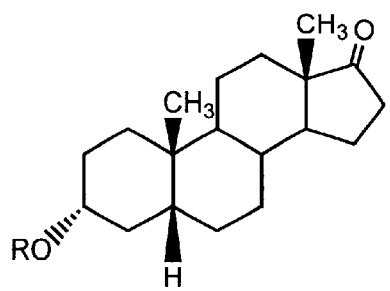
Figure 1:
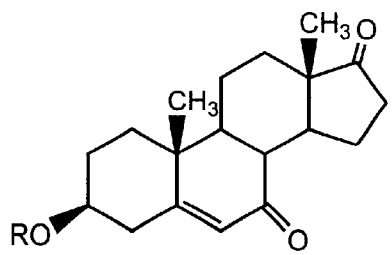

As used herein a "17-Ketosteroid" or "17-KS" refers to a mixture of the four different steroid metabolites: dehydroepiandrosterone (DHEA), androsterone, etiocholanolone and epiandrosterone. More specifically 17-KS refers to a mixture of the following 9 steroid metabolites: dehydroepiandrosterone sulfate (DHEA-S), 17-keto-DHEA-S, DHEA glucuronide (DHEA-G), androsterone-S, androsterone-G, etiocholanolone-S, etiocholanolone-G, epiandrostcrone-S and epiandrosterone-G. 17-KS consists mainly of 17-Keto-Steroid sulfates (17-KS-S) and 17-Keto-Steroid glucuronides (17-KS-G), the latter of which is derived from cortisol, DHEA and testosterone. The structures of these steroids is depicted in FIG. 1.

"17-Ketosteroid Sulfate" or "17-KS-S" refers to a mixture containing only the four ketosteroid sulfates: DHEA-S, androsterone-S, etiocholanolone-S and epiandrosterone-S.

"Anabolic/Catabolic Index" also referred to as the "ACI" refers to the ratio of 17-KS-S to creatinine in urine.

"Clinically derived standard range of 17-KS-S/ACI" refers to a range of ACI values that have been experimentally quantified by evaluating the ACI values of a large number of individuals of differing ages. Evaluation of such information provides ranges of values associated with specific age groups. See, for example, FIG. 4.

In one embodiment of the method of the present invention, chromatographic separation of the urinary 17 ketosteroids is followed by detection by mass spectrometry. The chromatographic separation can be preformed by high pressure liquid chromatography (HPLC) or by gas chromatography (GC). The method of the present invention can be illustrated schematically as follows:

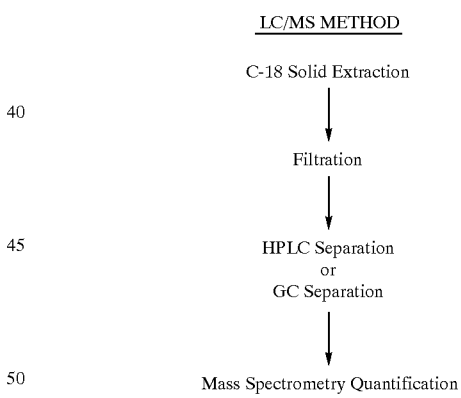

LC/MS METHOD

C-18 Solid Extraction

↓

Filtration

↓

HPLC Separation
or
GC Separation

↓

Mass Spectrometry Quantification

As can be seen in the scheme the method of the present invention comprises elution of a sample containing 17-KS-S through a reverse phase chromatography column, including but not limited to a C4, C8, C12 and C18 cartridge, followed by filtration of the eluted material. The filtered material is then separated by HPIC or GC and analyzed by mass spectrometry. This method is described in detail in Example 3. The advantages of this method over the current methods are that it is specific for 17 ketosteroid sulfates and it is a short process, involving only one extraction.

The method of this invention can be used to correlate 17 KS-S levels to biological age. Normal ranges of 17-KS-S, referred to herein as the "clinically derived standard range of 17-KS-S" have been established for different age groups, expanding the application of the ACI to reflect biological age. Comparison of the ACI of a person of a particular age group, to the clinically derived standard range of 17-KS-S, for that particular age group provides an indication of the biological age of that subject.

Additionally, as the data base increases, it is anticipated that important associations may be revealed between ACI levels and specific disease states. The ACI is also useful for a benchmark evaluation of healthy individuals. A variety of diet, lifestyle and nutritional supplement interventions can produce changes in hormones such as 17 KS-S, cortisol, catecholamines and insulin. Without having to conduct an entire battery of tests, the ACI appears to accurately reflect both positive and negative influences on this critical hormone balance.

The following examples are provided for illustrative purposes only and are not intended to limit the scope of the invention.

EXAMPLES

Reagents

Dehydroepiandrosterone-β-sulfate (DHEA-S), dehydroepiandrosterone-3-β-glucuronide (DHEA-G), epiandrosterone-3-β-sulfate, epiandrosterone-3-β-glucuronide, androsterone-3-β-sulfate, androsterone-3 -β-glucuronide, etiocholanol-17-one-3 -β-sulfate, etiocholanol-17-one-3-β-glucuronide were purchased from Sigma with >99% purity. 7-Keto-dehydro-epiandrosterone-3-β-sulfate pyridine salt was supplied by Dr. Henry Lardy from University of Wisconsin at Madison. ACS grade ammonium acetate, sodium hydrogenphosphate and sodium dihydrogenphosphate were purchased from Sigma. Acetonitrile (HPLC grade) and methanol (ACS grade) were purchased from Fisher. C18 Sep-Pak cartridges (Vac RC 500 mg) were purchased from Waters. 20% MeOH, m-dinitrobenzene (0.2% w/v in MeOH), tetramethylammonium hydroxide (TMAH, 2.7 mol/L in MeOH) and tetramethylammonium hydroxide (56 mmol/L in MeOH, color stabilizer) were purchased from Sigma Chemical Co.

$Na_2HPO_4/NaH_2PO_4$ buffer (0.067 M, pH 7.0) was prepared as follows: $NaH_2PO_4$ (9.5 g) was dissolved in 100 mL deionized (DI) water and $NaH_2PO_4$ (9.2 g) was dissolved in 100 mL Dl water. The pH of the $Na_2HPO_4$ was then adjusted to 7 with the $NaH_2PO_4$ solution and the resulting $Na_2HPO_4/NaH_2PO_4$ buffer was diluted to 10 times its volume. 50% $MeOH/CHCl_3$ saturated with NaCl was prepared by combining MeOH (1000 mL), $CHCl_3$ (1000 mL) and NaCl (30 g). DHEA-S stock solution (1 mg/mL) was prepared as follows: DHEA-S (25 mg) was dissolved in EtOH (25 mL) to provide a stock solution of DHEA-S (25 $\mu$g/mL).

Instrumentation

A Hitachi M-8000 ion trap mass spectrometer (LC-3DQ-MS) with sonic spray ionization source was utilized for the quantification at negative ionization mode. The LC/MS was calibrated with directed injection of 6 ng/$\mu$L of total 17-ketosteroid sulfates with a Harvard Apparatus, Inc. model 11 syringe pump at a flow rate of 100 $\mu$L/min. Unit mass resolution was established and maintained at ±0.3 m/z with a peak width of less than 2.50. Nitrogen gas was generated from a liquid nitrogen tank with an output pressure of 60 psi and an ion source inlet flow rate of 3.6 kgf/cm², and helium gas was utilized as buffer gas with an output pressure of 60 psi and an ion source inlet flow rate of 3.0 kgf/cm². The sonic ion source plate had a temperature of 275° C. with 1.0 kv voltage. Aperture temperatures were set up at 170° C. and 120° C., respectively. The draft voltage was 75 V and the focus voltage was 35 V. The ion accumulation time was 300 ms with a scan range of 300 to 500 m/z. The data were processed with a centroided format.

Chromatographic Conditions

The mobile phase solvents (an isocratic solution of 80% 0.2 mM ammonium acetate and 20% acetonitrile), were placed on the appropriate channels of the HPLC. The mobile phase was delivered with a Hitachi L-7100 gradient pump, through an Hitachi inline degassor at a flow rate of 0.4 $\mu$L/min. A Phenomenex Luna C-18 column (10.0×2.0 mm, 3 $\mu$m) was installed with a precolumn in an Hitachi L-7300 column oven and the temperature was set at 50° C. A Hitachi L-7200 sequential autosampler with a temperature setting at 5C was utilized to inject 20 $\mu$L, samples. The effluent from the column was transferred directly to a Hitachi M-8000 ion trap mass detector with a D-7000 interface module.

Example 1

Determination of 17-Ketosteroid Sulfates (17-KS-S ) in Urine-Colorimetric Method Preparation of a 17-KS-S Standard Calibration Curve for use with Calorimetric Method A 17-KS-S standard calibration curve was prepared as follows.

1. DHEA-S stock solution (25 $\mu$g/mL) (0, 100, 200, 400, 600 and 800 $\mu$L) was pipetted into six test tubes labeled 1–6 (corresponding to an amount of DHEA-S of 0, 2.5, 5, 10, 15 and 20 $\mu$g, respectively).

2. To each test tube was added m-dinitrobenzene (0.5 mL) and the mixtures were briefly vortexed.

3. The solvent in each test tube was then evaporated to dryness in a RapidVap at 37° C., using a vortex speed of 40 (about 15 minutes).

Note: Steps 4–9 should be completed for each pair of test tubes before proceeding to next pair.

4. To each test tube, was added tetramethylammonium hydroxide (0.5 mL), the residue was dissolved by vortexing vigorously and the solutions were allowed to stand at room temperature for 20 minutes.

5. After 20 minutes, n-BuOfl (1.0 mL) was added to each test tube and the mixtures were briefly vortexed.

6. To each test tube, was then added saturated NaCl aqueous solution (1.0 mL) and the mixtures were vortexed vigorously.

7. To each of six cuvets, labeled 1–6, respectively, was added color stabilizer (4 drops, 0.05 mL).

8. The n-BuOH layer (upper layer, step 6) was transferred into the cuvets prepared in Step 7 and the solutions were mixed well with a pipette.

9. The absorbance of each cuvet was read at 480, 520 and 560 nm vs EtOH as reference.

10. The calibration curve was then plotted using corrected absorbance values vs corresponding 17-KS-S ($\mu$g).

17-KS-S Analysis Procedures

A. C18 Sep-pak Solid Phase Extraction.

C18 sep-pak cartridges (500 mg, Waters) were conditioned by passing MeOH (5 $\mu$L) and 0.067 M phosphate buffer (5 mL) through them. Urine samples (5 mL) were mixed with buffer (5 mL) and applied to the conditioned C18 sep-pak cartridge (speed of elution should be less than 3 drops/second). Three preparations were prepared for each urine sample. Each cartridge was then rinsed with buffer (3 mL) and 20% MeOH (3 mL) and dried by vacuum for 5 minutes. Each cartridge was then eluted with MeOH (3 mL). The eluent was collected in a 20 mL scintillates vial. The solvent was removed in a RapidVap at 40° C. using a vortex speed of 40 (about 15 minutes).

B. LH1–20 Separation.

LH-20 columns were prepared by adding 8 mL of Sephadex LH-20 resin (swollen with 50% $MeOH/CHCl_3$ saturated with NaCl) into empty column cartridges (Bio-Rad). To each dried sample from the C18 solid phase extraction above, was added 50% MeOH/CHCl$_3$ saturated with NaCl (0.25 mL) and the residue was dissolved by mixing. The sample was then transferred to the LH-20 column. The column was then rinsed with 50% MeOH/CHCl$_3$ saturated with NaCl (11 mL), followed by washing with MeOH (15 mL). The eluent was collected in a 40 mL scintillates vial, which had been washed with 50% MeOH/CHCl$_3$ saturated with NaCl (3×0.25 mL).

C. Color Reaction and UV Measurement.

To each vial from step B was added m-dinitrobenzene (1.25 mL) and the samples were mixed by vortexing. The solvent was removed in a RapidVap at 40° C. using a vortex speed of 40 (about 30 minutes). Note: the remaining steps should be completed for each pair of tubes before proceeding to the next pair. To each vial, was added tetramethylammonium hydroxide (1.25 mL) and the residue was dissolved by vortexing vigorously. The vials were then allowed to stand at room temperature for 20 minutes. To each vial, was then added n-BuOH (2.5 mL), and the mixtures were vortexed briefly. Saturated aqueous NaCl solution (2.5 mL) was then added to each vial and the mixtures were vortexed vigorously. The n-BuOH layer (upper layer, about 1 mL) was then transferred into cuvets (1.5 mL) to which color stabilizer (4 drops, 0.05 mL) had been added. The solutions were mixed well with a pipette and the absorbance of each cuvet was read and recorded at 480, 520 and 560 nm vs EtOH as reference. The 17-KS-S content ($\mu$g) was then calculated using corrected absorbance values and calibration curve as depicted in the following equation.

$$17\text{-KS-S (mg/day)} = \frac{17\text{-KS-S }(\mu g)}{2\text{ mL}} \times \text{urine volume }(L)$$

Example 2
Determination of Creatinine in Urine at 500 nm Reagents

The sodium hydroxide solution (1.0 N), acid reagent (mixture of sulfuric acid and acetic acid), creatinine standard (3.0 mg/dL, 265 $\mu$mol/L) in hydrochloric acid (0.02 N) and creatinine color reagent were purchased from Sigma Chemical Co. The alkaline picrate solution was prepared by mixing the creatinine color reagent (5 volumes) with the sodium hydroxide solution (1 volume). This solution is stable at room temperature in the dark for one week.

Creatinine Analysis

A urine sample (1 volume) was mixed with water (14 volumes). To a cuvet was added water (0.3 mL) (blank solution), to a second cuvet was added the creatinine standard (0.3 mL) (standard solution), to a third cuvet was added the diluted urine (0.3 mL) (test solution). To all of the cuvets was added the alkaline picrate solution (3.0 mL). The samples were then mixed and allowed to stand at room temperature for 8–12 minutes. The absorbance (A) of the standard and test solutions vs the blank solution as a reference was measured at 500 nm (Initial A). To all of the cuvets was then added acid reagent (0.1 mL). The samples were mixed immediately and thoroughly and allowed to stand for 5 minutes at room temperature. The absorbance (A) of standard and test solutions vs the blank solution as reference was then measured at 500 rn (Final A). The creatinine concentration is calculated using the difference between Initial A and Final A as depicted in the following equation.

$$\text{Creatinine (g/day)} = \frac{\text{Initial }A_{Test} - \text{Final }A_{Test}}{\text{Initial }A_{Std} - \text{Final }A_{Std}} \times$$

$$3\text{ mg/dl} \times 15 \times \text{Urine volume }(L) \times 10$$

Example 3
Determination of 17-Ketosteroid Sulfates (17-KS-S in Urine-LC-MS Method Preparation of a 17-KS-S Standard Calibration Curve.

7-Keto-DHEA-S (12 mg), DHEA-G (4 mg), androsterone glucuronide (40 mg), DHEA-S (13 mg), epiandrosterone sulfate (0.5 mg), androsterone-sulfate (25 mg) and etiocholanolone sulfate (22 mg) were placed into a 100 mL volumetric flask. Boric acid (100 mg) was added and the mixture was dissolved in an appropriate volume of 22% acetonitrile in 0.2 mM ammonium acetate to yield a 600 ng/$\mu$L stock solution of total 17-KS-S. The stock solution was diluted in a 1:100 ratio with 22% acetonitrile in 0.2 mM ammonium acetate to generate an external standard at a concentration of 6 ng/$\mu$L. Serial dilution of the stock solution was performed to give calibration standards at level of 15, 9, 6, 1.5, 0.6, 0.3, 0.12 ng/$\mu$L of total 17-KS-S. The stability of the standards was measured after storage at −10° C. for 2 months. Each determination was performed in duplicate injections.

TABLE 1

17-KS-S Standard Calibration Curve Values

| 17-Ketosteroid | Linear Equation | Correlation Coefficient | Linearity Range |
| --- | --- | --- | --- |
| 7-Keto-DHEA-S | Y = 69172X | 0.9836 | 0.03–2.17 ng/$\mu$L |
| DHEA-G | Y = 332352X | 0.9959 | 0.01–0.92 ng/$\mu$L |
| Androsterone-3-$\beta$-glucuronides | Y = 354871X | 0.9886 | 0.08–6.08 ng/$\mu$L |
| DHEA-S | Y = 383924X | 0.9802 | 0.03–2.11 ng/$\mu$L |
| Epiandrosterone-3-$\beta$-sulfate | Y = 510530X | 0.9921 | 0.01–0.81 ng/$\mu$L |
| Androsterone-3-$\beta$-sulfate | Y = 402473X | 0.9725 | 0.05–3.92 ng/$\mu$L |
| Etiocholanolone-3-$\beta$-sulfate | Y = 392178X | 0.9802 | 0.05–3.66 ng/$\mu$L |

C18 Sep-pak Solid Phase Extraction.

C18 sep-pak cartridges (500 mg, Waters) were conditioned by passing MeOH (5 mL) and 0.067 M phosphate buffer (5 mL) through them. To a sample of urine (5 mL) was added buffer (5 ml) and the mixture was applied to the conditioned C18 sep-pak cartridge (speed of elution should be less than 3 drops/second). Three preparations were prepared for each urine sample. Each cartridge was then rinsed with deionized water (8 mL) and 30% MeOH (3 mL) and dried by vacuum for 5 minutes. The cartridge was then eluted with MeOH (4 mL). The eluent was collected and the solvent was removed in a RapidVap at 40° C. using a vortex speed of 40 (about 15 minutes). The volume was then adjusted to 5 mL by the addition of acetonitrile/buffer. The solution was then filtered through a 0.45 µm filter and the solution (1.8 mL) transferred to a 2 mL vial.

The solution was then applied to a HPLC column. The mobile phase solvents were delivered by a Hitachi L-7100 gradient pump through a Hitachi inline degasser at a flow rate of 0.4 mL/min. The mobile phase was composed of an isocratic solution of 0.1 M ammonium acetate:acetonitrile (75:25, v/v) at time t=0 to t=12.5; then the column was washed with deionized water:acetonitrile (25:75, v/v) at time t=12.6 to t=15.0. A 5.0 minute post run time was used to re-equilibrate the column.

Figure 2A:
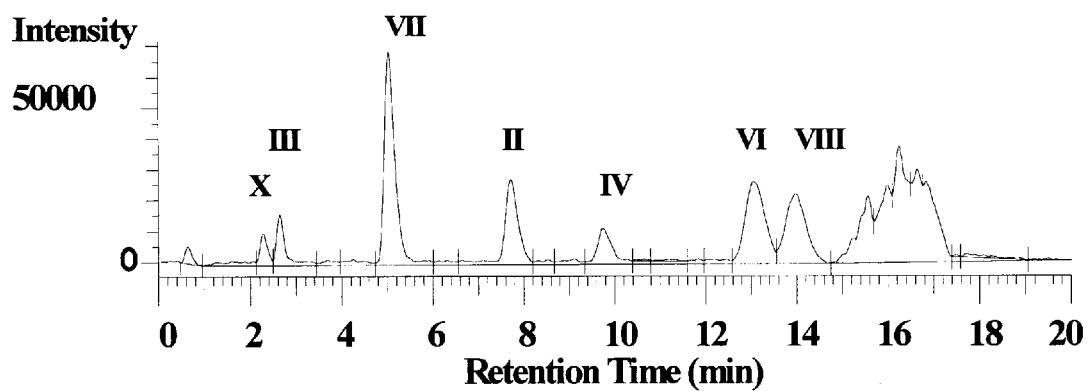
FIG. 2A shows the Total Ion Chromatogram (TIC) of seven 17-ketosteroid standards: (II) dehydroepiandrosterone-3-β-sulfate(DHEA-S, retention time (rt) 7.73 min.); (III) dehydroepiandrosterone-3-β-glucuronide(DHEA-G, rt 2.64 min.); (IV) epiandrosterone-3-β-sulfate, rt 9.72 min. (VI) androsterone-3-β-sulfate, rt 13.08 min.; (VII) androsterone-3-β-glucuronide, rt 5.04 min.; (VIII) etiocholanol-I7-one-3-β-sulfate, rt 13.98 min.; and (X) 7-keto-DHEA-S pyridine salt, rt 2.27 min.
Figure 2B:
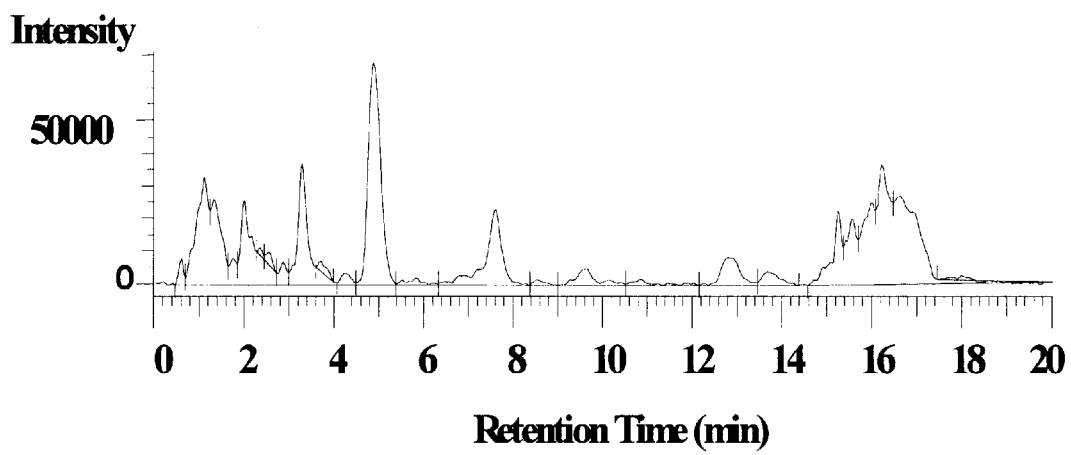
FIG. 2B shows the TIC of the 17-ketosteroids in a human urine sample.
Figure 2C:
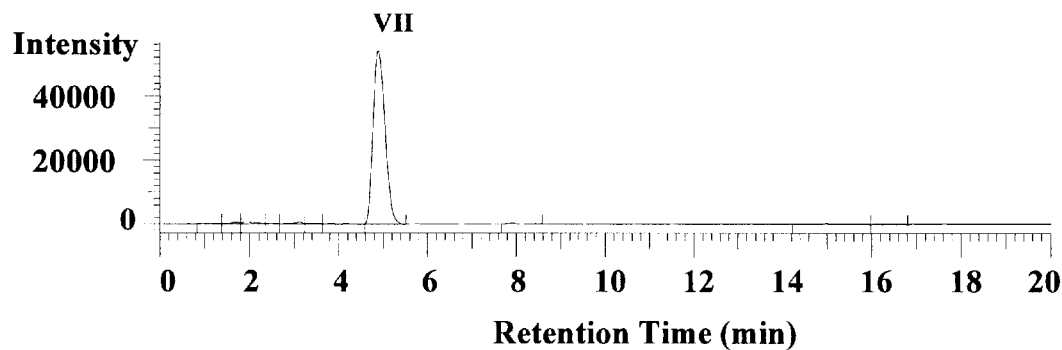
FIG. 2C shows the Select Ion Chromatogram (SIC) of a standard solution of (VII) androsterone-3 -β-glucuronide, MS m/z 465.
Figure 2D:
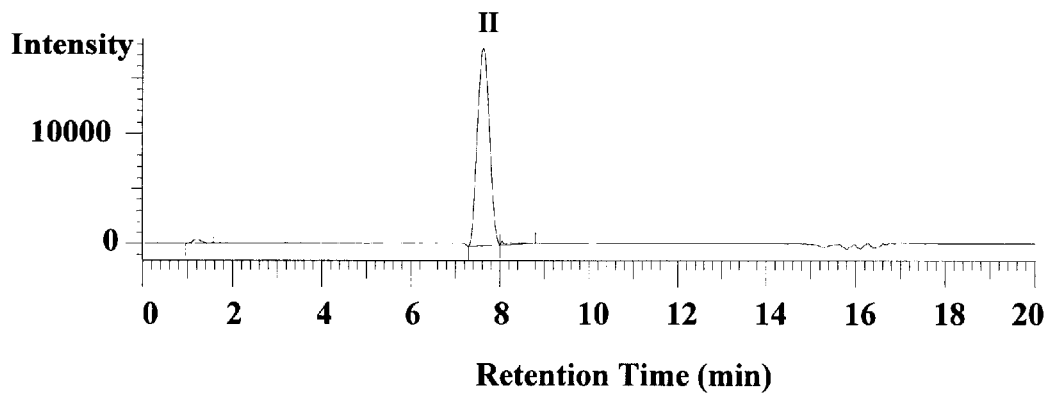
FIG. 2D shows the SIC of a standard solution of (II) DHEA-S, MS m/z 367.
Figure 2E:
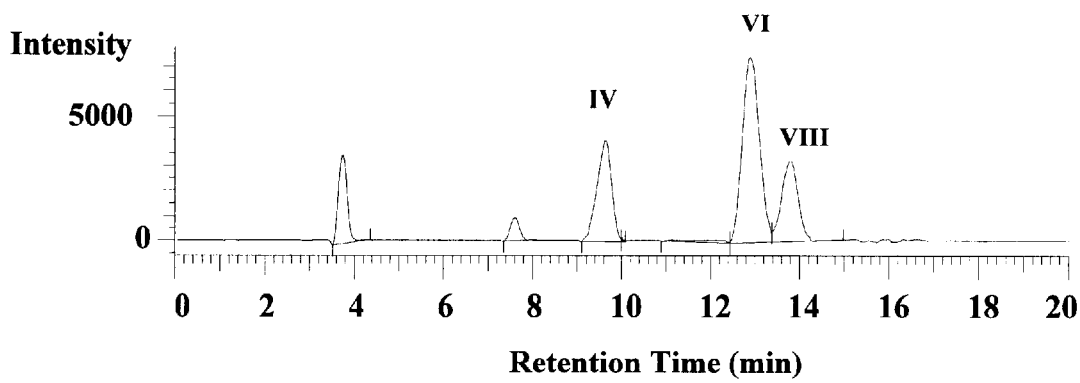
FIG. 2E shows the SIC of a mixture of a standard solution of (IV) epiandrosterone-3-β-sulfate, (VI) androstcrone-3-β-sulfate and (VIII) etiocholanol-17-one-3-β-sulfate; MS m/z 369.

All seven 17-ketosteroid standards were fully separated within twenty minutes using a C18 HPLC column (FIGS. 2A and B). Individual 17-ketosteroids were identified from the total ion chromatogram of urine specimens using select ion monitoring (FIGS. 2C–E).

The concentration of 17-KS-S in the sample was calculated from the ratio of the peak area of the compound of interest to that of the external standard multiplied by its concentration. The concentration of creatinine in urine was measured by a colorimetric method. The urinary Anabolic/Catabolic Index (ACI=X/Y) was calculated as a ratio of total 17-ketosteroid sulfate concentration (X,ng/µL) to creatinine concentration (Y, µg/µL).

Example 4

Human Clinical Trials

There were two objectives in this example. The first was to investigate the ACI-age relationship using baseline information of ACI and the second was to investigate effects of four treatment groups on ACI.

A. The Analysis Data Sets

There were 71 individuals for treatment allocation. They were identified with a number of 1 through 72 (69 was not used). Of these 71 individuals, five (subject identification numbers =3, 22, 24, 26 and 65) were not included in the data set of ACI measurements. Consequently, there were 66 individuals represented in the ACI information. Among the 66 individuals, three (subject ID=1, 9 and 60) had only baseline measurements. These three individuals contributed to the analysis of age/ACT relationship only. Therefore, the data set for looking at treatment effects consisted of 63 individuals. Not all of the 63 individuals have six serial observations. Subject 47 did not have ACI measurement at weeks 4 and 5.

B. ACI-AGE Relationship

Figure 3:
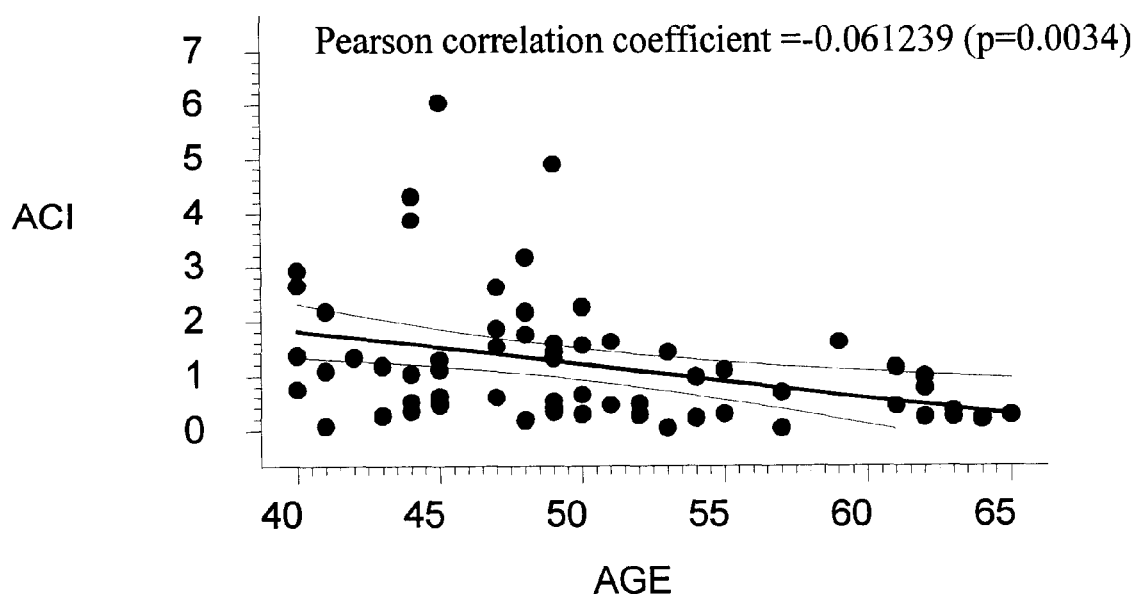
FIG. 3 shows the linear regression of baseline ACI on age, depicting ACI versus age.

There were 66 individuals in this data set, including 49 females and 17 males between the ages of 40 to 65. A 24-hour urine specimen was collected from each individual before treatment. The urine specimens were quickly aliquoted, frozen, and immediately shipped on dry ice by overnight service for analysis. A ratio of total 17-ketosteroid sulfate concentration (ng/µL) to creatinine concentration (mg/mL) was calculated and expressed as ACI. Subsequent to treatment urine specimens were collected and analyzed at 24 hours. FIG. 3 shows the linear regression result. The fitted line has a negative slope (estimate of the slope is—0.061239 and is statistically significant from zero with p-value being equal to 0.0034.). Pearson correlation is estimated to be—0.35510 (p=0.0034). These findings indicate that ACI level decreases with ages between 40 and 65.

ANCOVA analysis was performed to look at the gender effect while adjusting for age. Gender was found to be a non-significant factor in this analysis.

Figure 4:
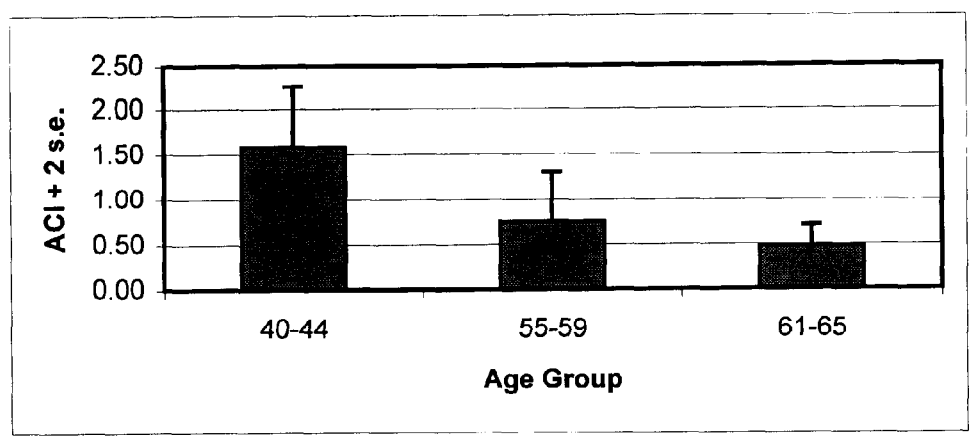
FIG. 4 is a bar graph depicting ACI versus age.

Table 2 and FIG. 4 show the summary statistics of ACI when ages are grouped with a 10 year interval (40–49, 50–59 and 60–65). Table 3 shows the results of the corresponding pair-wise comparisons. Even though the last two groups do not reach statistical significance by the conventional cutoff of p-value equal to 0.05, one should not reject the conclusion about the trend that ACI decreases with age.

TABLE 2

Summary statistics of ACI by age group

| Age Group | N | Mean | Standard | Standard error | Median |
| --- | --- | --- | --- | --- | --- |
| 40–49 | 37 | 1.58 | 1.41 | 0.23 | 1.27 |
| 50–59 | 19 | 0.80 | 0.64 | 0.15 | 0.65 |
| 60–65 | 10 | 0.48 | 0.35 | 0.11 | 0.30 |

TABLE 3

Pair-wise comparison by Wilcoxon Rank Sum Test

| Age Group | 40–49 | 50–59 | 60–65 |
| --- | --- | --- | --- |
| 40–49 | | 0.0286 | 0.0023 |
| 50–59 | | | 0.1614 |
| 60–65 | | | |

C. Treatment Effect

This part of the analysis was performed to determine if any of three different treatments affect the ACI level. That is to check whether the ACI level changes under and after termination of treatment. There were four treatment groups, referred to as groups 1–4. The individuals in Group 1 were given a placebo. The individuals in Group 2 were treated with 7-keto DHEA (25 mg/day dosage). The individuals in Group 3 were treated with Longevity Signal Formula (LSV) (2.008 mg/day dosage). The individuals in Group 4 were treated with Longevity Signal Formula (LSV)and Renewal lerbal Formula (Renewal).

1. The raw data

Figure 5:
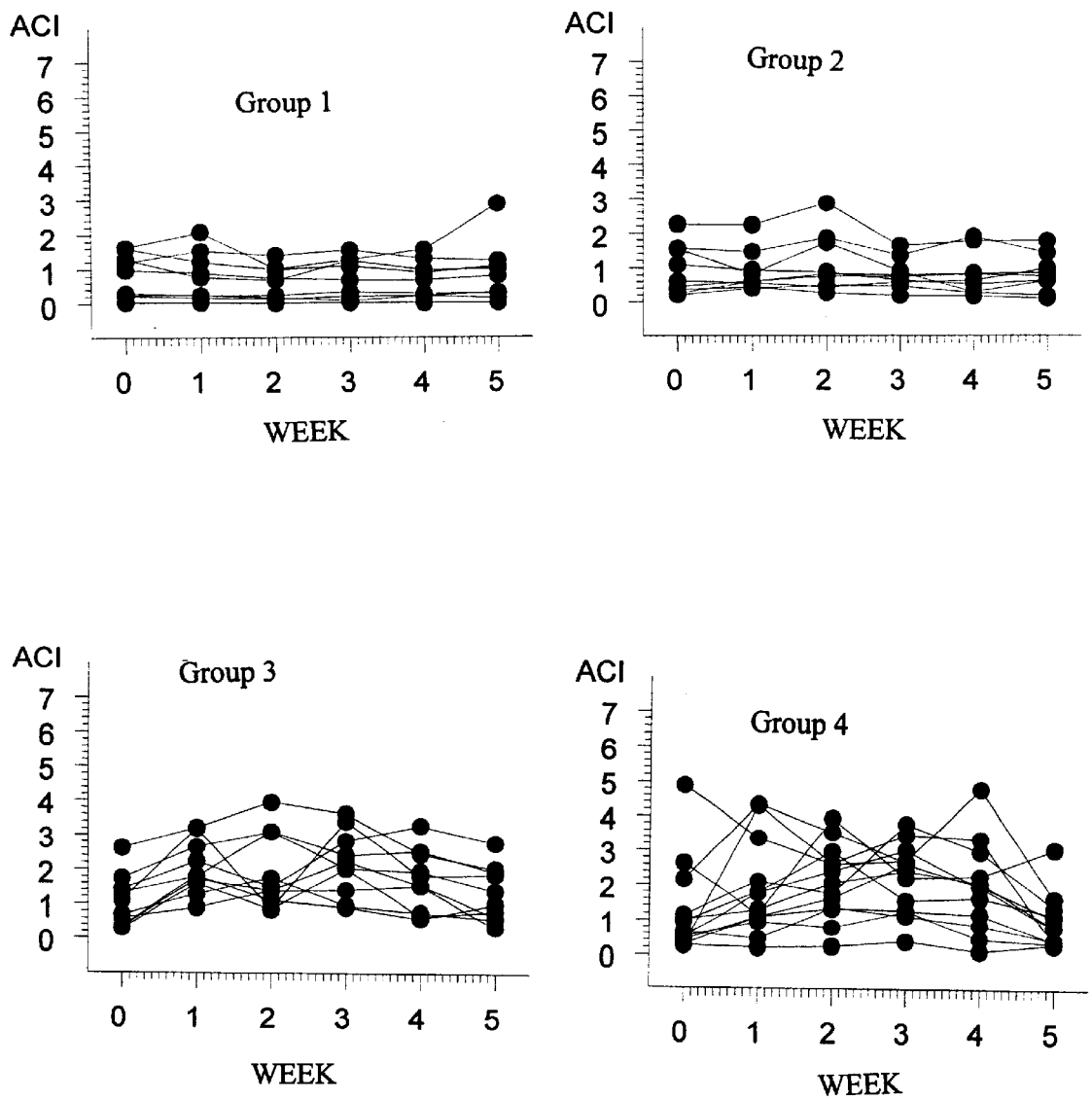
FIG. 5 shows the individual profiles for each of the four treatment groups, depicting ACI versus time.
Figure 6:
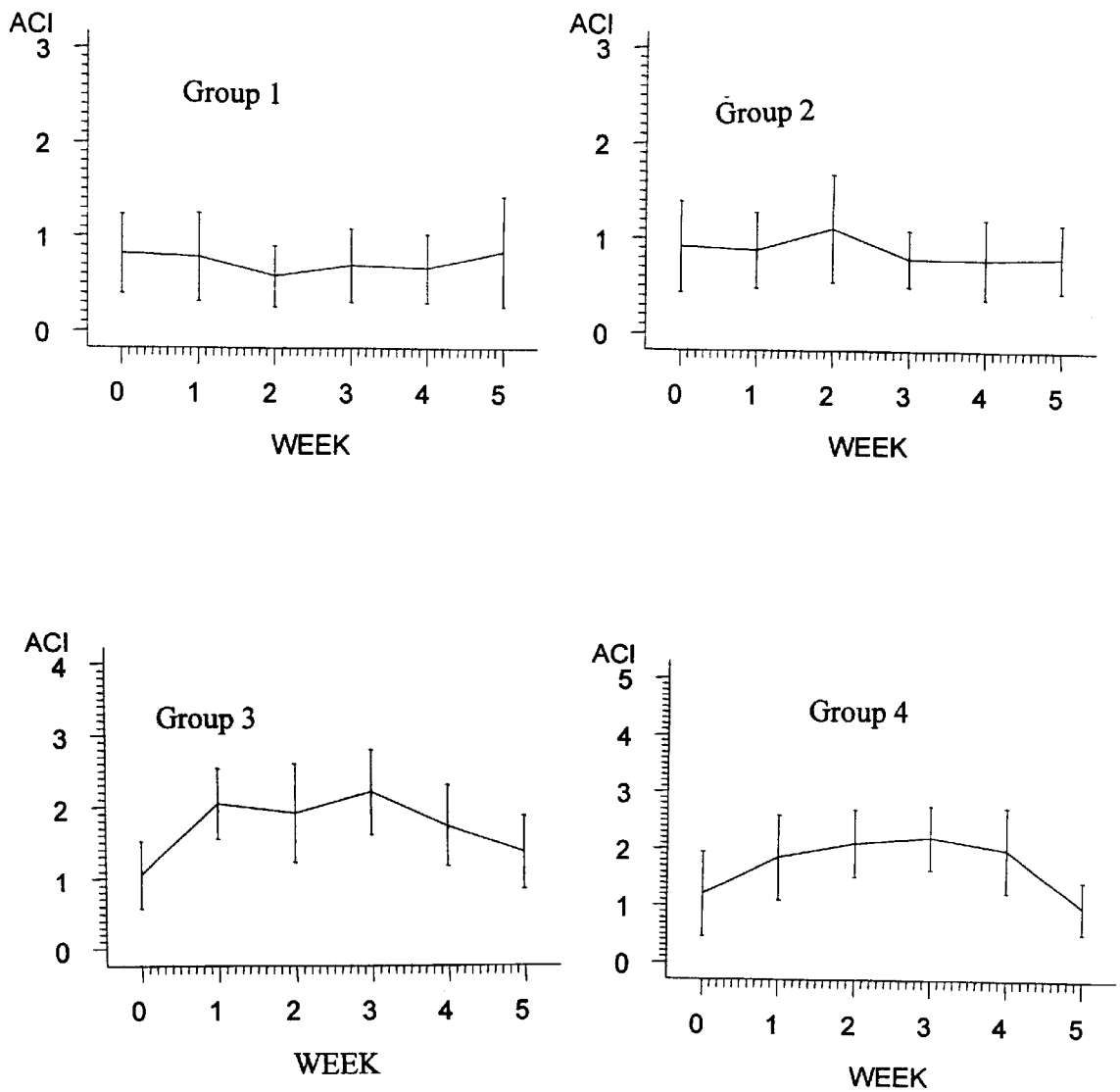
FIG. 6 shows the mean ACI versus time for each of the four treatment groups.

FIG. 5 illustrates the plots of the individual profile for each treatment group for weeks 1–5. Each individual's serial observations are connected with a line to emphasize the trend over time. Measurements at week zero represent ACI prior treatment. Measurements at weeks 1–4 represent the ACI level after receiving treatments for 1–4 weeks respectively. Measurements at week 5 represent the ACI level three days after termination of treatment. FIG. 6 plots the mean responses at each point in time plus two standard errors.

2. Effect of Treatment with a Placebo (Group 1)

The effect, on the ACI, of treatment with a placebo is illustrated in Table 4 and FIGS. 5 and 6. As can be seen in FIGS. 5 and 6, and Table 4 the ACI levels are consistently slightly lower under treatment than the baseline value. however, there is only a single pair-wise comparison (week 0 vs. week 2) which is statistically significant. In addition, the test of the null hypothesis that there are no changes in ACI from week 0 to week 5 cannot be rejected when analyzing the data with mixed effects model.

TABLE 4

*Pair-wise comparison results by paired t-test for Group 1 (placebo)*

| N | Mean of difference | S.e. | T | p-value | LCLM | UCLM | Comparison | Difference |
|---|---|---|---|---|---|---|---|---|
| 9 | −0.03 | 0.10 | −0.34 | 0.74 | −0.27 | 0.20 | week 0 vs. 1 | week 1 - week 0 |
| 9 | −0.24 | 0.10 | −2.39 | 0.04 | −0.47 | −0.01 | week 0 vs. 2 | week 2 - week 0 |
| 9 | −0.12 | 0.09 | −1.40 | 0.20 | −0.32 | 0.08 | week 0 vs. 3 | week 3 - week 0 |
| 9 | −0.15 | 0.08 | −1.81 | 0.11 | −0.34 | 0.04 | week 0 vs. 4 | week 4 - week 0 |
| 9 | 0.03 | 0.17 | 0.20 | 0.85 | −0.35 | 0.42 | week 0 vs. 5 | week 5 - week 0 |
| 9 | −0.20 | 0.11 | −1.82 | 0.11 | −0.46 | 0.05 | week 0 vs. 2 | week 2 - week 1 |
| 9 | −0.09 | 0.11 | −0.75 | 0.47 | −0.35 | 0.18 | week 1 vs. 3 | week 3 - week 1 |
| 9 | −0.11 | 0.07 | −1.55 | 0.16 | −0.28 | 0.06 | week 1 vs. 4 | week 4 - week 1 |
| 9 | 0.07 | 0.11 | 0.64 | 0.54 | −0.18 | 0.31 | week 1 vs. 5 | week 5 - week 1 |
| 9 | 0.12 | 0.06 | 1.87 | 0.10 | −0.03 | 0.26 | week 2 vs. 3 | week 3 - week 2 |
| 9 | 0.09 | 0.07 | 1.29 | 0.23 | −0.07 | 0.25 | week 2 vs. 4 | week 4 - week 2 |
| 9 | 0.27 | 0.21 | 1.32 | 0.22 | −0.20 | 0.75 | week 2 vs. 5 | week 5 - week 2 |
| 9 | −0.03 | 0.06 | −0.46 | 0.66 | −0.17 | 0.11 | week 3 vs. 4 | week 4 - week 3 |
| 9 | 0.15 | 0.19 | 0.81 | 0.44 | −0.28 | 0.59 | week 3 vs. 5 | week 5 - week 3 |
| 9 | 0.18 | 0.14 | 1.25 | 0.25 | −0.15 | 0.51 | week 4 vs. 5 | week 5 - week 4 |

3. Effect of Treatment with 7-keto DHEA (25 mg/day) (Group 2)

The effect on the ACI of treatment with 7-keto DFIEA is illustrated in FIGS. 5 and 6 Table 5 (Group 2). As can be seen in FIGS. 5 and 6, no trend is observed for this treatment group. The higher mean value of ACI at week 2 was associated with a higher variability. All pair-wise comparisons are not statistically significant. These findings were confirmed by the mixed effects model analysis. Therefore, it is possible to conclude that treatment with 7-keto DHEA does not change the ACI level at all. (See, Table 5).

powder (200:1) (60 mg), MaxCell (proprietary blend) (50 mg), 7-keto (3-acetyl-7-oxo dehydroepiandrosterone) (25 mg) and DHEA (dehydroepiandrosterone) (10 mg). As can be seen in FIGS. 5 and 6, the ACI on average increased and reached a maximum at week 3 while individuals were under treatment. After termination of treatment, the ACI dropped back. For example, 4 persons had ACI values lower at week 3 than week 2.

ACI levels under treatment are all statistically significant from the baseline. That is, the treatment increases ACI.

TABLE 5

*Pair-wise comparison results by paired t-test for Group 2*

| N | Mean of difference | S.e. | T | p-value | LCLM | UCLM | Comparison | Difference |
|---|---|---|---|---|---|---|---|---|
| 9 | −0.04 | 0.10 | −0.35 | 0.73 | −0.27 | 0.20 | week 0 vs. 1 | week 1 - week 0 |
| 9 | 0.20 | 0.10 | 1.90 | 0.09 | −0.04 | 0.43 | week 0 vs. 2 | week 2 - Week 0 |
| 9 | −0.12 | 0.14 | −0.83 | 0.43 | −0.44 | 0.21 | week 0 vs. 3 | week 3 - week 0 |
| 9 | −0.12 | 0.19 | −0.64 | 0.54 | −0.56 | 0.32 | week 0 vs. 4 | week 4 - week 0 |
| 9 | −0.10 | 0.16 | −0.65 | 0.53 | −0.47 | 0.26 | week 0 vs. 5 | week 5 - week 0 |
| 9 | 0.23 | 0.12 | 1.95 | 0.09 | −0.04 | 0.50 | week 1 vs. 2 | week 2 - week 1 |
| 9 | −0.08 | 0.09 | −0.95 | 0.37 | −0.28 | 0.12 | week 1 vs. 3 | week 3 - week 1 |
| 9 | −0.09 | 0.12 | −0.74 | 0.48 | −0.36 | 0.18 | week 1 vs. 4 | week 4 - week 1 |
| 9 | −0.07 | 0.10 | −0.68 | 0.51 | −0.30 | 0.16 | week 1 vs. 5 | week 5 - week 1 |
| 9 | −0.31 | 0.15 | −2.07 | 0.07 | −0.66 | 0.04 | week 2 vs. 3 | week 3 - week 2 |
| 9 | −0.32 | 0.19 | −1.71 | 0.13 | −0.75 | 0.11 | week 2 vs. 4 | week 4 - week 2 |
| 9 | −0.30 | 0.18 | −1.71 | 0.13 | −0.70 | 0.11 | week 2 vs. 5 | week 5 - week 2 |
| 9 | −0.01 | 0.10 | −0.05 | 0.96 | −0.24 | 0.23 | week 3 vs. 4 | week 4 - week 3 |
| 9 | 0.01 | 0.07 | 0.19 | 0.86 | −0.15 | 0.18 | week 3 vs. 5 | week 5 - week 3 |
| 9 | 0.02 | 0.08 | 0.23 | 0.82 | −0.17 | 0.21 | week 4 vs. 5 | week 5 - week 4 |

4. Effect of Treatment with LSF (2008 mg/day) (Group 3)

The effect on ACI of treatment with LSF is illustrated in FIGS. 5 and 6 and Table 6. LSF is a nutritional complex designed to activate anabolic activity. Daily dosage of LSF includes four capsules each capsule containing: iron (0.05 mg), 1-arginine HCl (99%) (963 mg), lyelum barbarum (fruit extract) (20% amino acids) (400 mg), chlorella (whole plant powder) (300 mg), Fo-ti (Polygonum multiform (cured root extract) (12:1) (200 mg), Aloe vera (spray dried gel Although the ACI levels at week five were observed to be higher than the baseline, this difference did not reach statistical significance. Also, the under-after treatment comparisons were significant or close to being, significant. These findings indicate that the teartment effect subsided soon after the withdrawal of treatment.

There is no statistical significance for any pair-wise comparisons under treatment. In other words, the fluctuations of ACI under treatment are not statistically different.

TABLE 6

Pair-wise comparison results by paired t-test for Group 3

| N | Mean of difference | S.e. | T | p-value | LCLM | UCLM | Comparison | Difference |
|---|---|---|---|---|---|---|---|---|
| 10 | 1.00 | 0.18 | 5.69 | 0.00 | 0.60 | 1.39 | week 0 vs. 1 | week 1 - week 0 |
| 10 | 0.86 | 0.19 | 4.47 | 0.00 | 0.43 | 1.30 | week 0 vs. 2 | week 2 - week 0 |
| 10 | 1.16 | 0.22 | 5.28 | 0.00 | 0.66 | 1.66 | week 0 vs. 3 | week 3 - week 0 |
| 10 | 0.69 | 0.20 | 3.44 | 0.01 | 0.24 | 1.14 | week 0 vs. 4 | week 4 - week 0 |
| 10 | 0.32 | 0.19 | 1.65 | 0.13 | −0.12 | 0.76 | week 0 vs. 5 | week 5 - week 0 |
| 10 | −0.13 | 0.33 | −0.40 | 0.70 | −0.88 | 0.62 | week 1 vs. 2 | week 2 - week 1 |
| 10 | 0.16 | 0.17 | 0.94 | 0.37 | −0.23 | 0.56 | week 1 vs. 3 | week 3 - week 1 |
| 10 | −0.31 | 0.27 | −1.13 | 0.29 | −0.92 | 0.31 | week 1 vs. 4 | week 4 - week 1 |
| 10 | −0.68 | 0.19 | −3.51 | 0.01 | −1.11 | −0.24 | week 1 vs. 5 | week 5 - week 1 |
| 10 | 0.30 | 0.37 | 0.81 | 0.44 | −0.53 | 1.12 | week 2 vs. 3 | week 3 - week 2 |
| 10 | −0.17 | 0.32 | −0.55 | 0.60 | −0.89 | 0.54 | week 2 vs. 4 | week 4 - week 2 |
| 10 | −0.54 | 0.34 | −1.59 | 0.15 | −1.32 | 0.23 | week 2 vs. 5 | week 5 - week 2 |
| 10 | −0.47 | 0.22 | −2.12 | 0.06 | −0.97 | 0.03 | week 3 vs. 4 | week 4 - week 3 |
| 10 | −0.84 | 0.20 | −4.13 | 0.00 | −1.30 | −0.38 | week 3 vs. 5 | week 5 - week 3 |
| 10 | −0.37 | 0.16 | −2.38 | 0.04 | −0.72 | −0.02 | week 4 vs. 5 | week 5 - week 4 |

5. Effect of Treatment with LSF and Renewal System (Group 4)

The effect of treatment with a combination of LSF and Renewal System (Group 4) is set forth in Table 7 and FIGS. 5 and 6. From FIGS. 5 and 6, it can be seen that group 4 has a similar response pattern as that of Group 3. The ACI level increased gradually after treatment and reached a maximum at week 3 and then dropped back after the cessation of treatment.

Statistical comparison results for Group 4 are also similar to those of Group 2 (Table 7). Pair-wise comparisons between baseline and time points under treatment are statistically significant except for the pair between baseline and week 1. There are no differences in ACI under treatment. ACI level after cessation of treatment is not statistically significant from the baseline, but statistically significantly lower than measurements at weeks 2–4.

Consequently, one can conclude that the use of treatment with a combination of LSF and Renewal formula increases the ACI level, but the effect disappears soon after the discontinuation of the treatment.

SUMMARY

A review of the data makes the following findings clear:
1. ACI levels decrease slowly with age. The trend of decrease is statistically significant
2. There is no statistically significant change in ACI under treatment with the placebo.
3. The ACI has significant higher values under treatment than the baseline and drops back after discontinuation of treatment with LSF and a combination of LSF and the Renewal System.
4. For the groups treated with LSF and a combination of LSF and the Renewal System, the observed maximum ACI occurred at week 3. However, there is no statistical significance between measurements during medication.

Example 5

AM ACI Results

This analysis included individuals whose ages were 30 years and older. There were 807 individuals included in this analysis, 362 females and 445 males. The urine samples were collected between 8:00 and 10:00 AM and delivered and processed as described above in Example 4.

TABLE 7

Pair-wise comparison results by paired t-test for Group 4 (LSF + Renewal)

| N | Mean of difference | S.e. | T | p-value | LCLM | UCLM | Comparison | Difference |
|---|---|---|---|---|---|---|---|---|
| 13 | 0.64 | 0.40 | 1.60 | 0.14 | −0.23 | 1.52 | week 0 vs. 1 | week 1 − week 0 |
| 13 | 0.91 | 0.33 | 2.79 | 0.02 | 0.20 | 1.61 | week 0 vs. 2 | week 2 − week 0 |
| 13 | 1.01 | 0.41 | 2.49 | 0.03 | 0.13 | 1.89 | week 0 vs. 3 | week 3 − week 0 |
| 12 | 0.87 | 0.30 | 2.93 | 0.01 | 0.22 | 1.52 | week 0 vs. 4 | week 4 − week 0 |
| 12 | −0.12 | 0.30 | −0.42 | 0.68 | −0.77 | 0.53 | week 0 vs. 5 | week 5 − week 0 |
| 13 | 0.26 | 0.31 | 0.86 | 0.41 | −0.41 | 0.93 | week 1 vs. 2 | week 2 − week 1 |
| 13 | 0.37 | 0.28 | 1.31 | 0.21 | −0.24 | 0.97 | week 1 vs. 3 | week 3 − week 1 |
| 12 | 0.36 | 0.21 | 1.70 | 0.12 | −0.10 | 0.82 | week 1 vs. 4 | week 4 − week 1 |
| 12 | −0.64 | 0.39 | −1.63 | 0.13 | −1.50 | 0.22 | week 1 vs. 5 | week 5 − week 1 |
| 13 | 0.10 | 0.28 | 0.37 | 0.72 | −0.51 | 0.72 | week 2 vs. 3 | week 3 − week 2 |
| 12 | 0.01 | 0.31 | 0.02 | 0.99 | −0.69 | 0.70 | week 2 vs. 4 | week 4 − week 2 |
| 12 | −0.99 | 0.19 | −5.17 | 0.00 | −1.41 | −0.57 | week 2 vs. 5 | week 5 − week 2 |
| 12 | −0.18 | 0.23 | −0.77 | 0.46 | −0.69 | 0.33 | week 3 vs. 4 | week 4 − week 3 |
| 12 | −1.17 | 0.31 | −3.74 | 0.00 | −1.86 | −0.48 | week 3 vs. 5 | week 5 − week 3 |
| 12 | −0.99 | 0.34 | −2.93 | 0.01 | −1.74 | −0.25 | week 4 vs. 5 | week 5 − week 4 |

Regression Analysis—ACI in Relation to Age and Gender

Figure 7:
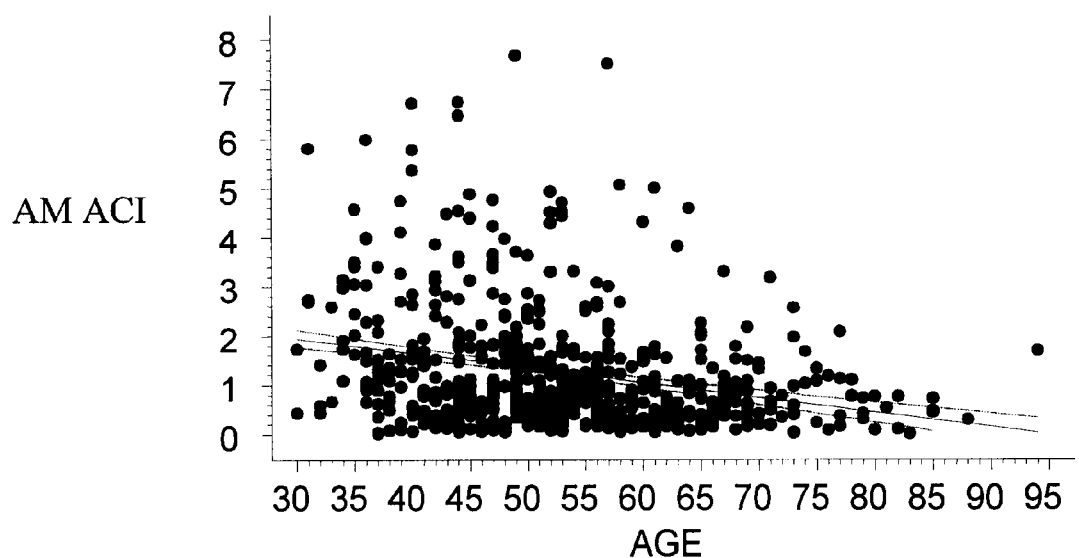
FIG. 7 shows the fitted linear regression of AM ACI based upon the age of the individual.

FIG. 7 shows the fitted linear regression lines of ACI based upon the age of the individual. The solid line is the fitted regression line and the two dashed lines are the 95% confidence interval for the true regression line. The estimated linear functions are: ACI=2.8–0.03*Age. The estimated slopes were negative indicating ACI decreases with age and were statistically significant from zero with p-value being equal to 0.0001.

ANCOVA was performed to look at gender and age effect. The interaction term was not statistically significant with p-value being equal to 0.7556. Gender is a statistically significant factor with p-value being equal to 0.0009. Specifically, males tend to have higher values of ACI for a given age than females as shown in FIG. 8.

ACI in relation to Age Group

Figure 8:
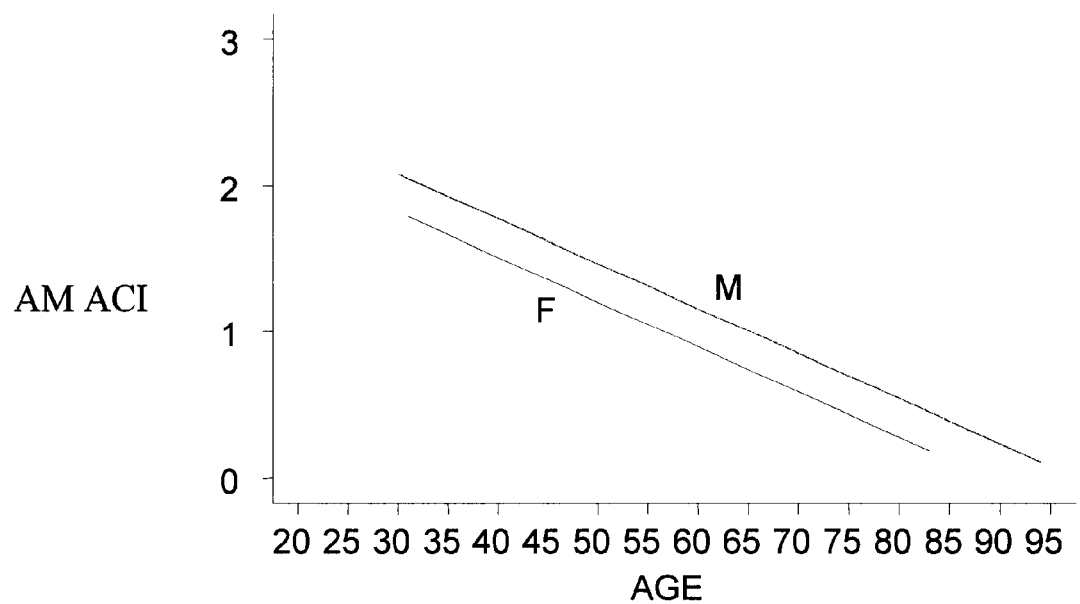
FIG. 8 illustrates the effect of gender on AM ACI.
Figure 9:
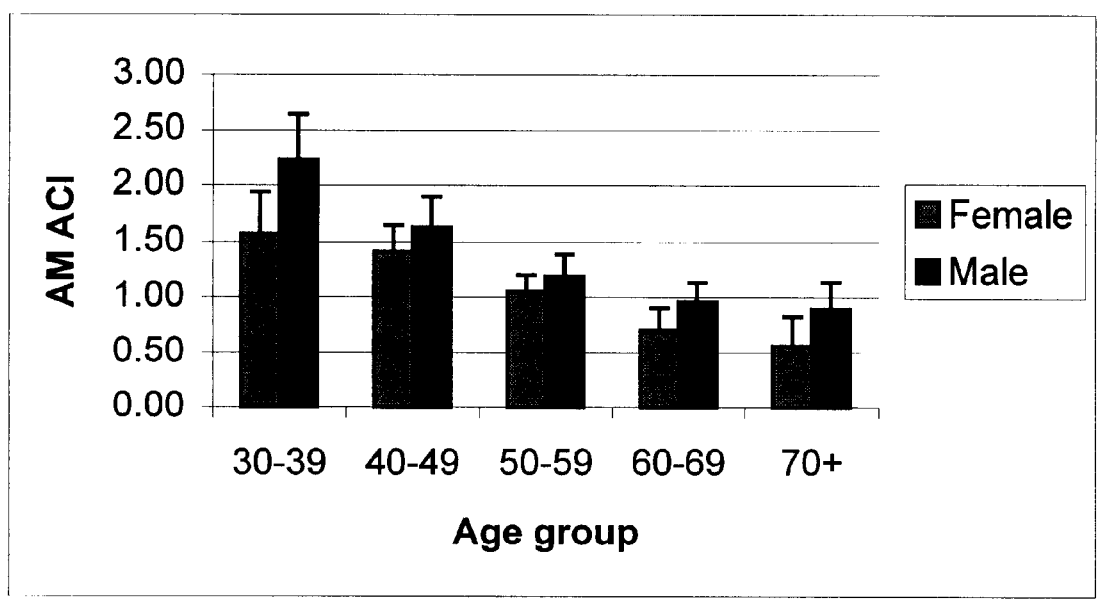
FIG. 9 shows a bar graph of AM ACI versus age for both males and females.

Table 8 and FIG. 8 show the mean AM ACI by age broken down into 10-year intervals for males and females, respectively. Review of this table and figure shows the decreasing trend of ACI with respect to age. Tables 9 and 10 show p-values of pair-wise comparisons by t-tests.

TABLE 8

ACI comparison by age group and gender

| GENDER | AGE_GRP | N | MEAN | STD | STDERR | MEDIAN |
|---|---|---|---|---|---|---|
| F | 30–39 | 39.00 | 1.57 | 1.13 | 0.18 | 1.32 |
| F | 40–49 | 111.00 | 1.40 | 1.32 | 0.12 | 0.96 |
| F | 50–59 | 124.00 | 1.05 | 0.83 | 0.07 | 0.84 |
| F | 60–69 | 67.00 | 0.71 | 0.79 | 0.10 | 0.45 |
| F | 70+ | 20.00 | 0.56 | 0.59 | 0.13 | 0.40 |
| M | 30–39 | 46.00 | 2.23 | 1.38 | 0.20 | 1.91 |
| M | 40–49 | 120.00 | 1.63 | 1.45 | 0.13 | 1.13 |
| M | 50–59 | 157.00 | 1.19 | 1.21 | 0.10 | 0.80 |
| M | 60–69 | 82.00 | 0.96 | 0.83 | 0.09 | 0.83 |
| M | 70+ | 40.00 | 0.90 | 0.78 | 0.12 | 0.64 |

TABLE 9

Pair-wise comparison results by paired t-test for females

| Age group | 30–39 | 40–49 | 50–59 | 60–69 | 70+ |
|---|---|---|---|---|---|
| 30–39 | | 0.4702 | 0.0105 | 0.0001 | 0.0001 |
| 40–49 | | | 0.0175 | 0.0001 | 0.0001 |
| 50–59 | | | | 0.0059 | 0.0125 |
| 60–69 | | | | | 0.4522 |
| 70+ | | | | | |

TABLE 10

Pair-wise comparison results by paired t-test for males

| Age group | 30–39 | 40–49 | 50–59 | 60–69 | 70+ |
|---|---|---|---|---|---|
| 30–39 | | 0.0166 | 0.0000 | 0.0001 | 0.0001 |
| 40–49 | | | 0.0081 | 0.0001 | 0.0001 |
| 50–59 | | | | 0.0775 | 0.0608 |
| 60–69 | | | | | 0.7007 |
| 70+ | | | | | |

SUMMARY

A review of the data makes the following findings clear:
1. AM ACI is negatively correlated with age and this correlation is statistically significant.
2. Males on average have higher AM ACI values of than females and the difference is also statistically significant.

What is claimed is:

1. A method for determining the biologic age of a person comprising:

a) determining the anabolic/catabolic index (ACI) of a population of individuals of different ages whereby standard ranges of ACI are quantified for various age groups; and b) determining the ACI of said person and comparing this value with said standard ranges of ACI for various age groups, correlating the ACI of said person with the biologic age of said person;

whereby said ACI is determined by the ratio of total urinary 17 ketosteroid sulfate levels (17-KS-S) over total urinary creatininie levels.

2. A method for monitoring the effects of a medical treatment on the biological age of a person comprising:

a) determining the anabolic/catabolic index (ACI) of said person prior to initiation of said medical treatment;

b) initiation of said medical treatment; and c) determining the ACI of said person at predetermined times during and subsequent to said medical treatment, correlating the ACI of said person with the biological age of said person as a result of said medical treatment;

whereby said ACI is determined by the ratio of total urinary 17 ketosteroid sulfate levels (17-KS-S) over total urinary creatinine levels.

3. A method of identifying medical treatments that affect the biological age of treated individuals comprising:

a) determining the anabolic/catabolic index (ACI) of a population of individuals prior to initiation of a preselected medical treatment;

b) initiation of said medical treatment to at least a portion of said population of individuals; and c) determining the ACI of said population of individuals at predetermined times during and subsequent to said medical treatment;

d) correlating the effect on the ACI of each individual to the effect on the biological age of the treated individual;

e) identifying said medical treatment as result of said correlation;

whereby said ACI is determine by the ratio of total urinary 17 ketosteroid sulfate levels (17-KS-S) over total urinary creatinine levels.

4. The method of claim 3 wherein a portion of the said population of individuals is not subjected to said medical treatment, and the differences in ACI levels in individuals receiving said medical treatment is compared to the differences in ACI levels in individuals not receiving said medical treatment to determine if the medical treatment is statistically significantly lower of the biological age of treated individuals.

* * * * *